United States Patent
Allen

(10) Patent No.: US 6,534,057 B2
(45) Date of Patent: *Mar. 18, 2003

(54) METHOD INCREASING THE DELAYED-TYPE HYPERSENSITIVITY RESPONSE BY INFUSING LFA-1-SPECIFIC ANTIBODIES

(76) Inventor: Allen D. Allen, 4236 Longridge Ave., Penthouse 302, Studio City, CA (US) 91604

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/940,228

(22) Filed: Sep. 30, 1997

(65) Prior Publication Data

US 2001/0006638 A1 Jul. 5, 2001

Related U.S. Application Data

(60) Division of application No. 08/467,356, filed on Jun. 6, 1995, now abandoned, which is a continuation of application No. 08/302,113, filed on Sep. 7, 1994, now Pat. No. 5,424,066, which is a continuation of application No. 08/165,751, filed on Dec. 13, 1993, now abandoned, which is a continuation-in-part of application No. 08/033,405, filed on Mar. 19, 1993, now abandoned.

(51) Int. Cl.$^7$ ........................ A61K 39/395; C07K 16/28
(52) U.S. Cl. ................... 424/154.1; 424/130.1; 424/141.1; 424/143.1; 424/144.1; 424/153.1; 424/173.1; 530/387.1; 530/388.1; 530/388.2; 530/388.22; 530/388.7; 530/388.73; 530/388.75
(58) Field of Search ............. 424/152.1, 130.1, 424/141.1, 153.1, 143.1, 154.1, 144.1, 173.1; 530/388.7, 388.85, 388.2, 388.73, 387.1, 388.22, 388.75, 388.1

(56) References Cited

U.S. PATENT DOCUMENTS

| | | | |
|---|---|---|---|
| 5,002,869 A | | 3/1991 | Schlossman et al. |
| 5,424,066 A | * | 6/1995 | Allen |
| 5,629,162 A | * | 5/1997 | DeFougerolles et al. |
| 5,651,970 A | | 7/1997 | Allen |

FOREIGN PATENT DOCUMENTS

| | | | | |
|---|---|---|---|---|
| WO | WO 90/13281 | * | 11/1990 | |
| WO | WO 94/21295 | | 11/1994 | ......... A61K/39/395 |

OTHER PUBLICATIONS

Valentin, A. et al. J. Immunol. 144 (3): 934–937, Feb. 1990.*

Busso, M. et al. AIDS 5 (12): 1425–1432, Dec. 1991.*

Kalter, D. C. et al. Immunol. Letters 30 (2): 219–227, Oct. 1991.*

Springer, T. A. Nature 346:425–434, Aug. 1990.*

Allen, A.D., et al., "Immunization against the HIV–associated anti–self, anti–CD4 cytotoxic T lymphocyte," AIDS, vol. 7, No. 8, 1993, pp. 1130–1131.

Autran, et al., "T Cell Receptor Gamma/Delta Lymphocyte Subsets During HIV–1 Infection", *Clin. Exp. Immunol.*, 1989; 72:206–10.

Brodie, Scott J., et al., "In vivo migration and function of transferred HIV–1–specific cytotoxic T cells," Nature Medicine, vol. 5, No. 1, Jan. 1999, pp. 34–41.

Butini, et al., "Intercellular adhesion molecules (ICAM)–1, ICAM–2 and ICAM–3 function as counter–receptors for lymphocyte function–associated molecule 1 in human immunodeficiency virus–mediated syncytia formation", *Eur. Journal of Immunology,* 1994, vol. 24, pp. 2191–2195.

Colvin, Robert B., et al., "Laboratory Monitoring of Therapy with OKT3 and Other Murine Monoclonal Antibodies," Clinics in Laboratory Medicine, vol. 11, No. 3, Sep. 1991, pp. 693–714.

De Fougerolles, Antonin R., et al., "Characterization of the Function of Intercellular Adhesion Molecule (ICAM)–3 and Comparison with ICAM–1 and ICAM–2 in Immune Response," J. Exp. Med., vol. 179, Feb., 1994, pp. 619–629.

DePaoli, et al., "A Subset of Gamma Delta Lymphocytes is Increased During HIV–Infection", *Clin. Exp. Immunol.,* 1991; 83:187–91;.

Desroches, Claudine Vermot, et al., "Leukocyte Function–Associated Antigen–1 Expression on Peripheral Blood Mononuclear Cell Subsets in HIV–1 Seropositive Patients," Clinical Immunology and Immunopathology, vol. 56, 1990, pp. 159–168.

Diegel, Michael L., et al., "Regulation of HIV Production by Blood Mononuclear Cells from HIV–Infected Donors : II, HIV–1, Production Depends on T Cell–Monocyte Interaction," AIDS Research and Human Retroviruses, vol. 9, No. 5, 1993. pp. 455–464.

Fecondo, John V., et al., "Synthetic Peptide Analogs of Intercellular Adhesion Molecule 1 (ICAM–1) Inhibit HIV–1 Replication in MT–2 Cells," AIDS Research and Human Retroviruses, vol. 9, No. 8, 1993. pp. 733–740.

(List continued on next page.)

*Primary Examiner*—Phillip Gambel
(74) *Attorney, Agent, or Firm*—Staas & Halsey LLP

(57) ABSTRACT

Methods for treating and inhibiting disease and symptoms associated with the human immunodeficiency virus (HIV) are provided. The method includes transforming the human immunodeficiency virus (HIV) infection into a nonserious disease through the infusion of monoclonal antibodies directed against particular antigens on anti-self, anti-CD4 cytotoxic T-lymphocytes. The monoclonal antibodies are primarily directed against the alpha or beta chain of LFA-1.

1 Claim, 11 Drawing Sheets

OTHER PUBLICATIONS

Fortin, Jean–Francois, et al., "Role of the Leukocyte Function Antigen–1 Conformational State in the Process of Human Immunodeficiency Virus Type 1–Mediated Syncytium Formation and Virus Infection," Virology, vol. 257, 1999, pp. 228–238.

Fortin, Jean–Francois, et al., "Interaction between Virion–Bound Host Intercellular Adhesion Molecule–1 and the High–Affinity State of Lymphocyte Function–Associated Antigen–1 on Target Cells Reners R5 and X4 Isolates of Human Immunodeficiency Virus Type 1 More Refractory to Neutralization," Virology, vol. 268, 2000, pp. 493–503.

Goldstein, G., "Overview of the Development of ORTHO-CLONE OKT3: Monoclonal Antibody for Therapeutic Use in Transplantation," Transplantation Proceedings, vol. XIX, No. 2, Suppl. 1, Apr. 1987, pp. 1–6.

Handzel, Z.T., et al., "Immunoreconstitution of T–Cell Impairments In Asymptomatic Male Homosexuals By Thymic Humoral Factor (THF)," Int. J. Immunopharmac, vol. 9, No. 2, pp. 165–173, 1987.

Harris, et al., TIBTECH, 11:42, 1993, "Therapeutic Antibodies—The Coming of Age,".

Hermier, et al., Decreased Blood TcRgd⁻ Lymphocytes in AIDS and p2Y–Antigenemic HIV–1 Infected Patients, *Clin. Immunol. Immunopathol.*, 1993; 69:248–250.

Hioe, Catarina E., et al., "Role of Cellular Adhesion Molecules in HIV Type 1 Infection and Their Impact on Virus Neutralization," AIDS Research and Human Retroviruses, vol. 14, Supplement 3, 1998, pp. S–247–S–254.

Houghton, Alan N., et al., "Monoclonal Antibodies: Potential Applications to the Treatment of Cancer," Seminars in Oncology, vol. 13, No. 2, Jun. 1986, pp. 165–179.

Kendall, Marion D., "Functional anatomy of the thymic microenvironment," J. Anat. (1991), 177, pp. 1–28.

Klimas, Nancy, et al., "Clinical and Immunological Changes in AIDS Patients Following Adoptive Therapy with Activated Autologous CD8 T Cells and Interleukin–2 Infusion", AIDS 1994, 8:1073–1081.

Klimas, Nancy, et al., Clinical Impact of Adoptive Therapy with Purified CD8 Cells in HIV Infection, Science, 234:1563–1566, 1986.

Lands, Lark, "Behind the Eight Ball, CD8 cells take center stage as research aims for remission", POZ Magazine, Feb. 1999.

Margolick, et al., "Flow Cytometric Analysis of Gamma–Delta T Cells and Natural Killer Cells in HIV–1 Infection", *Clin. Exp. Immunol.*, 1991: 58:126–138.

Matloubian, Mehrdad, et al., "CD8– T Cell Mediated Hematopoietic Dysfunction In Chronic Viral Infection," First Annual UCLA AIDS Institute Symposium, Oct. 27, 1992, p. 56.

Milman, Gregory, et al., "HIV–Mediated Defects in Immune Regulation," AIDS Research and Human Retroviruses, vol. 10, No. 4, 1994, pp. 421–430.

Morimoto, C., et al., "A Novel Epitope of the LFA–1 Antigen Which Can Distinguish Killer Effector and Suppressor Cells in Human CD8 Cells," Nature, Dec. 3, 1987, vol. 330, pp. 479–482.

Muul, "Current Status of Polymerase Chain Reaction Assays In Clinical Research of Human Immunodeficiency Virus Infection", *AIDS Updates*, 1990; 3: No. 4, 1–19.

Ng, Tony T.C., et al., "Adhesion co–receptor expression and intracellular signaling in HIV disease: implications for immunotherapy," AIDS, vol. 9, No. 4, 1995, pp. 337–343.

Patarca, Roberta, et al., "CD8 T–Cell Immunotherapy in AIDS : Rationale and Lessons Learned at the Cellular and Molecular Biology Levels", 1994 Elsevier Science Inc., 0197–1859/94/50.00–7.00.

Reisfeld, Ralph A., "Monoclonal Antibodies in Cancer Immunotherapy," Clinics in Laboratory Medicine, vol. 12, No. 2, Jun. 1992, pp. 201–216.

Scalise, et al., "Lymphocytes Bearing the Gamma–Delta T–Cell Receptor in Acute Toxoplasmosis", *Immunology*, 1992; 76: 668–70.

Scheglovitova, O., et al., "Antibody to ICAM–1 mediates enhancement of HIV–1 infection of human endothelial cells," Archives of Virology (1995) 140, pp. 951–958.

Shier, Peter, et al., "Defective CD8+ T Cell Activation and Cytolytic Function in the Absence of LFA–1 Cannot Be Restored by Increased TCR Signaling," Journal of Immunology, 1999, pp. 4826–4832.

Stein, Daniel S., et al., "Immune–Based Therapeutics : Scientific Rationale and the Promising Approaches to the Treatment of the Human Immunodeficiency Virus–Infected Individual," Clinical Infectious Diseases, Oct. 17, 1993, pp. 749–765.

Tedla, et al., "Phenotypic and functional characterization of lymphocytes derived from normal and HIV–1–infected human lymph nodes," Clin. Exp. Immunol., vol. 117, 1999, pp. 92–99.

Trainin, Nathan, "Prospects of AIDS Therapy by Thymic–Humoral Factor, a Thymic Hormone," Nat. Immun. Cell Growth Regul. 1990:9, pp. 155–159.

Tsubota, Hiroshi, et al.. "A Cytotoxic T Lymphocyte Inhibits Acquired Immunodeficiency Syndrome Virus Replication in Peripheral Blood Lymphocytes," J. Exp. Med., Apr. 1989, vol. 169, pp. 1421–1434.

Zarling, Joyce M., et al.. "HIV–Infected Humans, But Not Chimpanzees, Have Circulating Cytotoxic T Lymphocytes That Lyse Uninfected CD4+ Cells," The Journal of Immunology, vol. 144, No. 8, Apr. 15, 1990, pp. 2992–2998.

* cited by examiner

Changes in Circulating T Lymphocytes

Placement of antigens and control on forearm for Multitest CMI ®, a skin test to measure delayed hypersensitivity reaction.

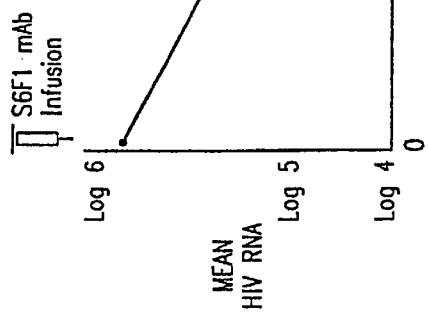

*FIG. 4A*

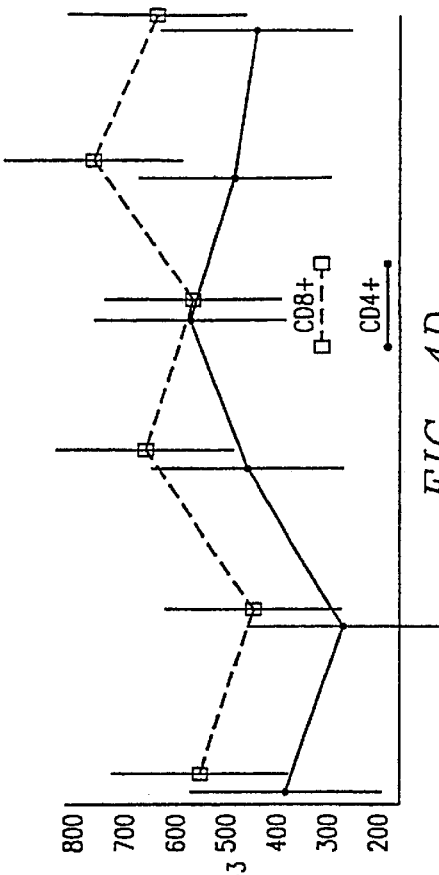

*FIG. 4C*

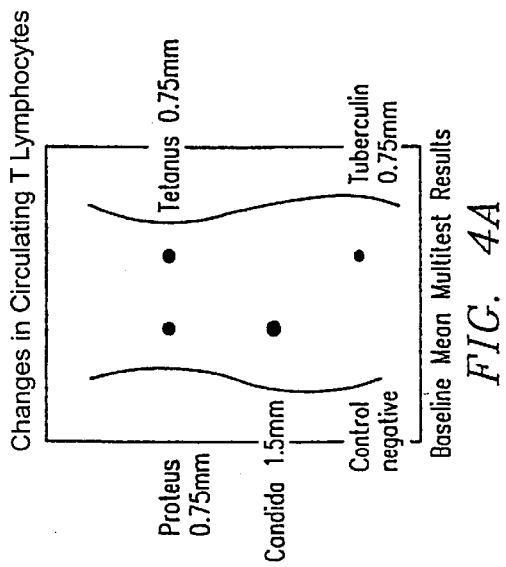

*FIG. 4B*

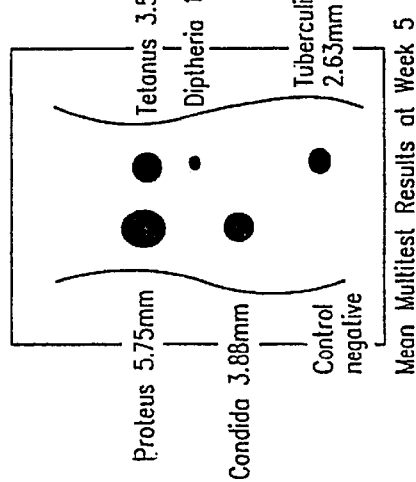

*FIG. 4D*

FIG. 4 Arithmetic mean of changes in blood tests for 5 patients who received S6F1 mAb, but not IL-2 or THF, and changes in skin reactivity multitest for 4 patients with baseline CD4 counts > 200 cells mm⁻³. Note that viral RNA is suppressed and delayed cutaneous hypersensitivity is improved at week 5 although T cell counts are not significantly different from baseline. This suggests an improvement in cell function.

Changes in Circulating T Lymphocytes

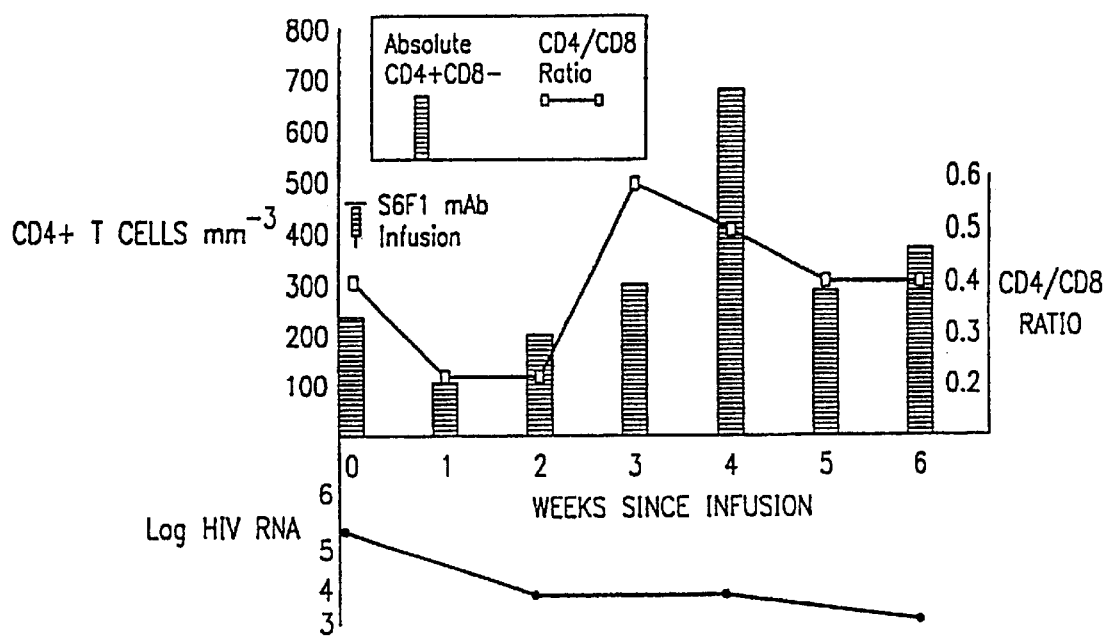

(a) 47-year-old male naive to all other therapies

FIG. 5A

FIG. 5 Results for 4 patients who entered study with baseline absolute CD4 count > 200 cells mm$^{-3}$. Changes in CD4/CD8 ratios preclude changes in circulating T cells due to cells trafficking in and out of tissue. Chronic bartonellosis can not be ruled out as the cause of the double-negative cells shown in (c). Disappearance of double-marked cells in (d) is in contrast to patients with later disease and suggests healthier lymphatic architecture.

(b) 47-year-old male taking a variety of investigational drugs (c) 51-year old male taking AZT (d) 43-year-old male taking a variety of investigational drugs

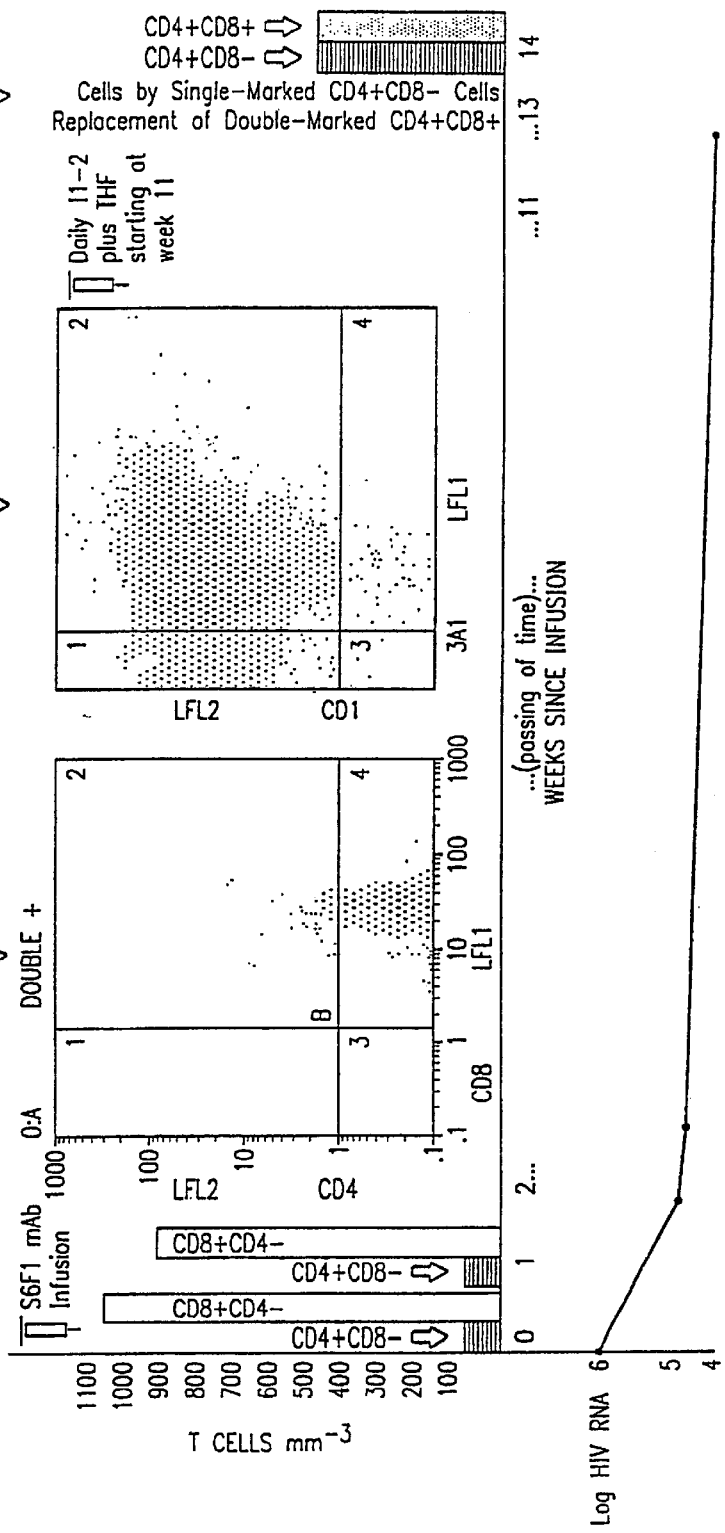
FIG. 6 32-year old male taking ddI. This patient had no single-marked CD8+ T cells for > 3 months without clinical consequence. IL-2 alone did not shift the CD4:CD8 histogram left to single-marked cells but THF alone did so in another patient.

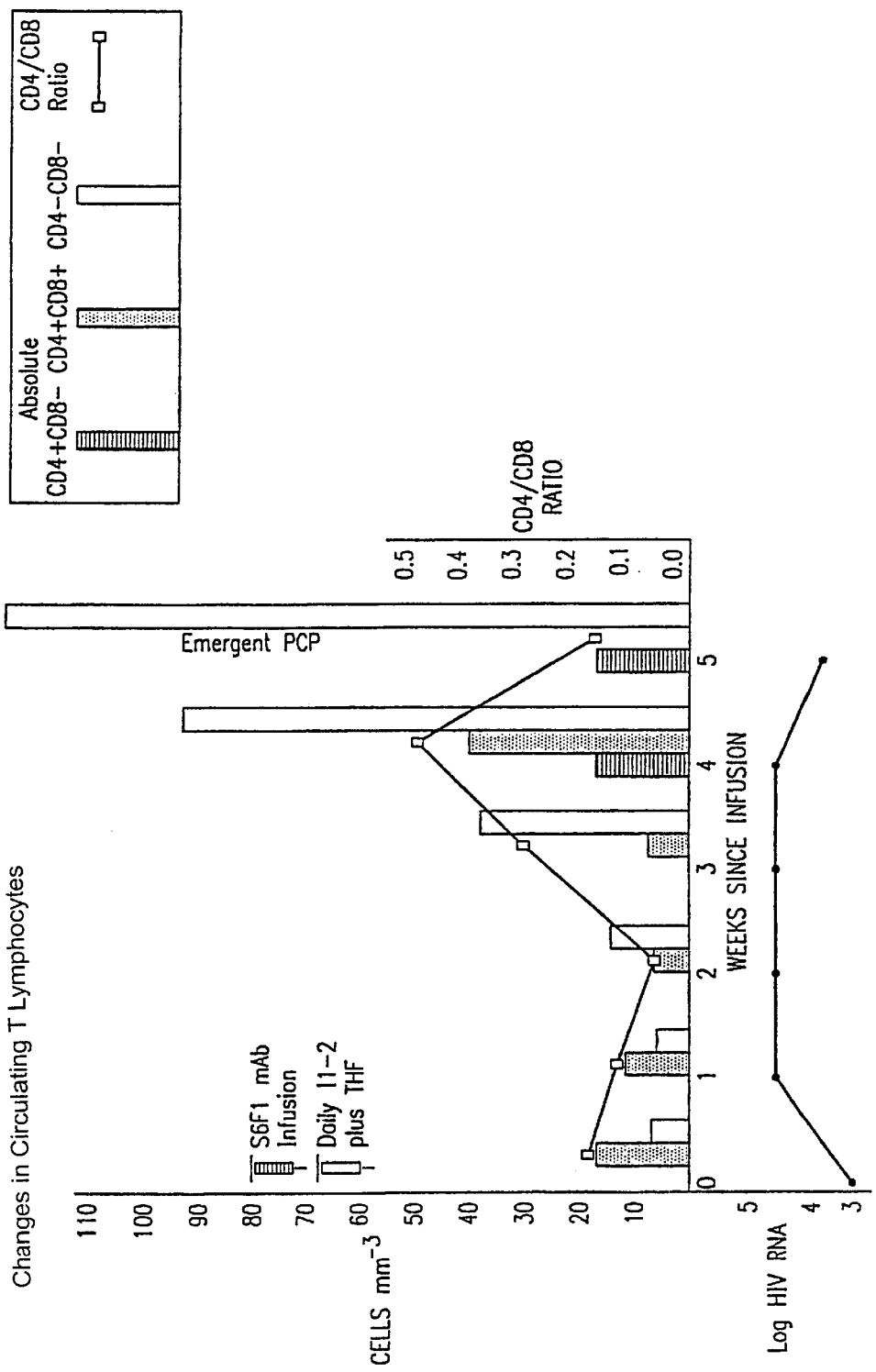

FIG. 7 26-year old male taking AZT and a variety of investigational drugs. The diagnosis of PCP illustrates the association between double-negative cells and secondary infections, and suggests that these cells may not offer much protection against opportunistic infections. The increase in viral RNA may be secondary to rIL-2. Appearance of a modicom of single marked CD4 cells at week 4 suggests that the effects of HIV-impaired lymphatic architecture can be ameliorated.

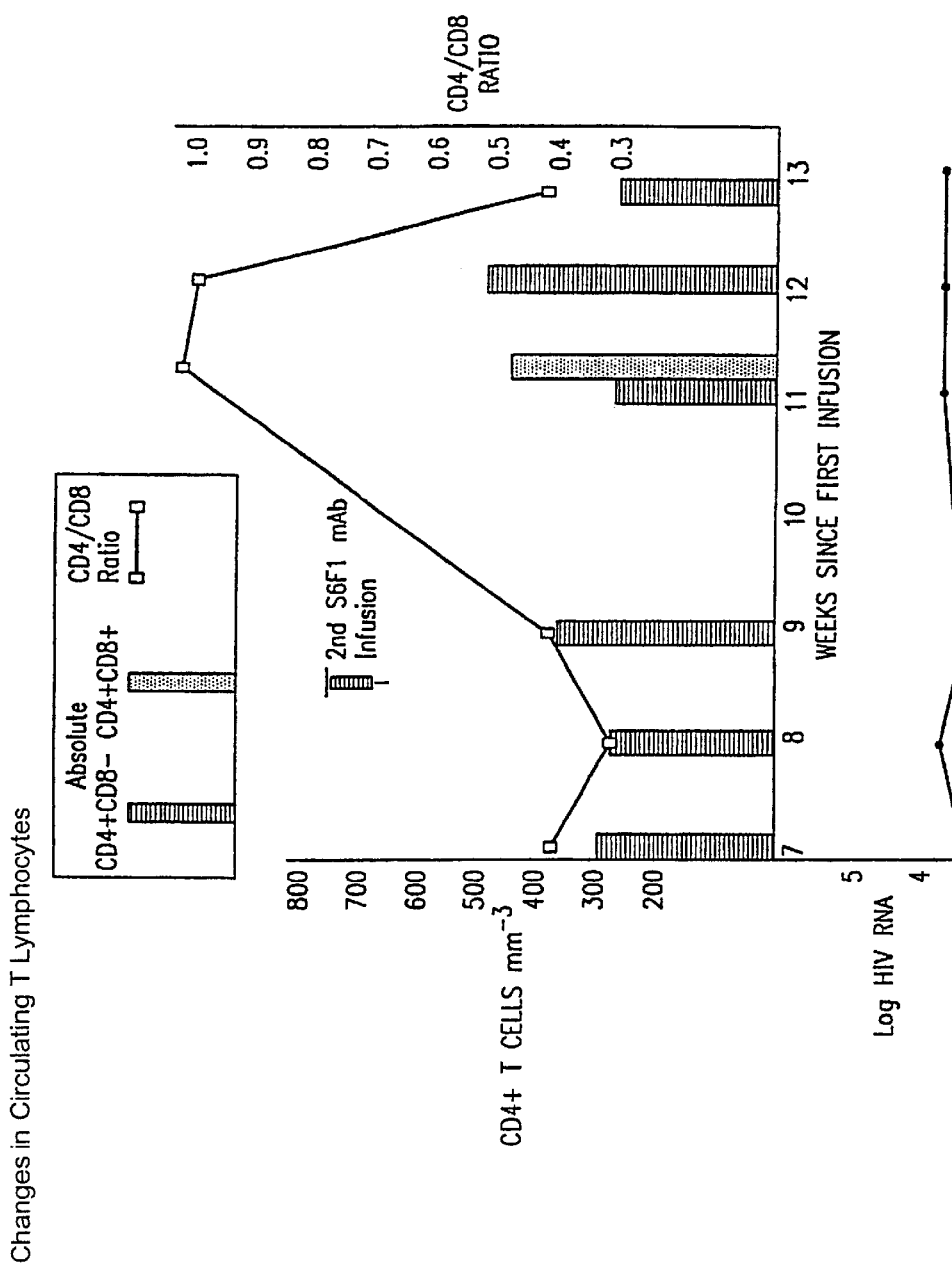
FIG. 8 Response to second infusion of 7 mg S6F1 MAb. This illustrates that the effect of infusion is reproducible in a patient, and that infusion does not increase circulating CD4 cells by exhausting tissue reserves.

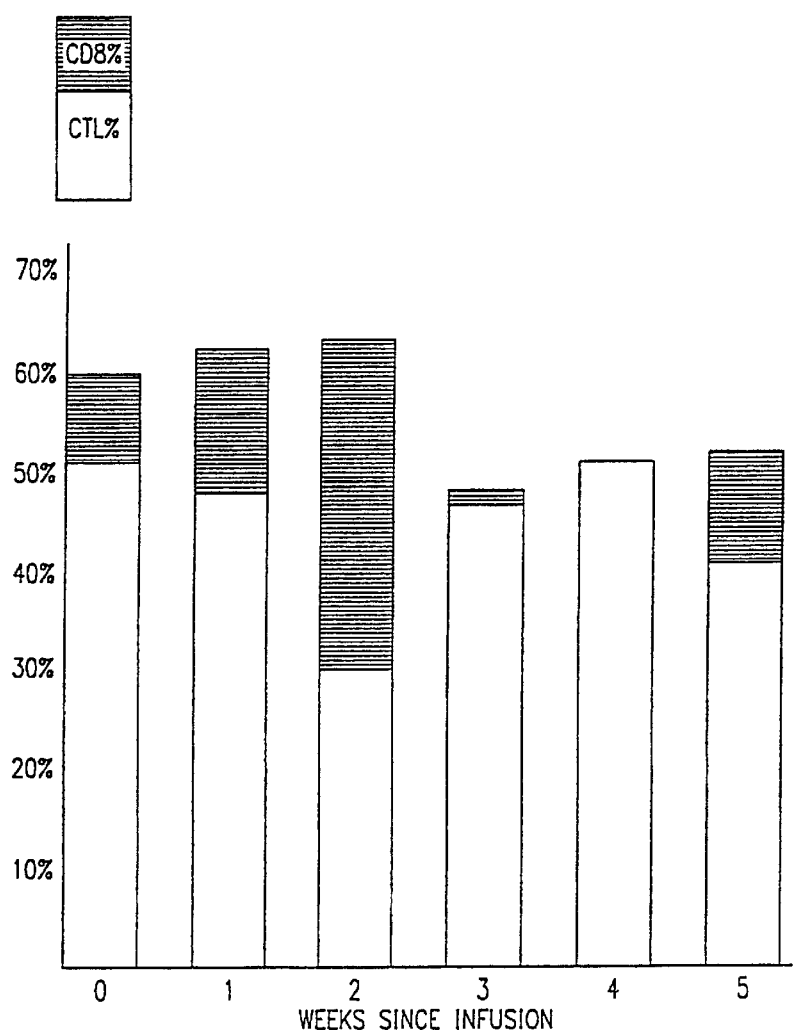
FIG. 9 Arithmetic mean of CD8% and CTL% of T cells for 5 patients who had single-marked CD8+ T cells. This illustrates that either (a) the prolonged effects of S6F1 MAb infusion are not related to ephemeral changes in CTL count, or (b) the immune system is mathematically chaotic.

METHOD INCREASING THE DELAYED-TYPE HYPERSENSITIVITY RESPONSE BY INFUSING LFA-1-SPECIFIC ANTIBODIES

CROSS REFERENCE TO RELATED APPLICATIONS

This application is related to U.S. Ser. No. 08/437,745, filed Jun. 7, 1995, now U.S. Pat. No. 5,651,970.

This application is a division of U.S. Ser. No. 08/467,356, filed Jun. 6, 1995, now abandoned, which was a continuation of U.S. Ser. No. 08/302,113, filed Sep. 7, 1994, now U.S. Pat. No. 5,424,066, which was a continuation of U.S. Ser. No. 08/165,751, filed Dec. 13, 1993, now abandoned, which was a continuation-in-part of U.S. Ser. No. 08/033,405, filed Mar. 19,1993, now abandoned.

BACKGROUND OF THE INVENTION

1. Technical Field

The present invention relates generally to methods for treating human disease conditions associated with the human immunodeficiency virus (HIV) and more particularly to the use of monoclonal antibodies directed against anti-self cytotoxic T-lymphocytes or their lytics in order to inhibit or treat HIV and related HIV diseases.

2. Description of the Related Art

Several viruses produce latent infection in humans and can reactivate to produce recrudescent or persistent disease. One such disease is the human immunodeficiency virus (HIV). HIV is associated with a progressive catastrophic disease in certain primates, including humans. Humans infected with HIV experience proliferation of a certain class of white blood cells known as cytotoxic T-lymphocytes (CTL). The final stage of this disease is commonly known as acquired immune deficiency syndrome (AIDS).

It is well known in the art that the clinical signs and symptoms of AIDS are primarily due to a profound loss of all lymphocytes marked with the CD3 and CD4 antigens (CD4+ T-lymphocytes). It is also generally accepted that the infectious agent in AIDS is the human immunodeficiency virus (HIV). Although HIV infects and destroys CD4+ cells, the number of cells infected is inadequate to account for the profound and indiscriminate loss of these cells that occurs in individuals infected with HIV. It has been suggested by those in the field that autoimmunity may play a role in the pathogenesis of AIDS. However, few have suspected a pathogenic cytotoxic T-lymphocyte (CTL).

Rather, it is generally accepted by those skilled in the art that CTL's are beneficial for those infected with HIV since it is believed CTL's help control the infection, i.e., CTL's are believed to be prognosticators that delay the progression of AIDS. Klimas, et al., "Phase I Trial of Adoptive Therapy with Purified CD8 Cells in HIV Infection", Int. Conf. AIDS, Jul. 19–24, 1992; Abstract No. PoB 3446, for example, have described infusion of CTL's into the bloodstream of HIV-infected patients as an experimental method of treatment. This particular type of infusion was directed to the mitogen-expanded colonies of the host patient's autologous CD8+ cells, a lymphocyte population that includes CTL's.

However, Zarling, et al, "HIV-Infected Humans, But Not Chimpanzees, Have Circulating Cytotoxic T-Lymphocytes That Lyse Uninfected CD4+ Cells", *J. Immunol.* 1990; 144: 2992–98 have shown that HIV-infected humans have an anti-self, anti-CD4 CTL in their circulating blood that lyses healthy, uninfected CD4+ cells. No such CTL was found in the blood of HIV-seronegative humans. Moreover, no such CTL or suicide cell was found in the blood of HIV-infected chimpanzees. This is significant because HIV infection manifests as a nonpathogenic colonization in the blood and tissue of chimpanzees.

T cell-monocyte adhesion pathways are important in HIV replication. Diegel. et al, "Regulation of HIV Production by Blood Mononuclear Cells from HIV Infected Donors: II. HIV-1 Production Depends on T Cell-Monocyte Interaction", *AIDS Res. Hum. Retroviruses,* 1993; 9:465–73 teach that blocking of either CD2-LFA-3 or CD18-ICAM-1 results in greater than 90% inhibition of HIV-1 production stimulated by anti-CD3 or staphylococcal enterotoxin/superantigen. Inhibition of HIV production, but not inhibition of CD4+ T lymphocyte proliferation, was observed when either the T cell or monocyte coreceptor was bound by monoclonal antibodies to these adhesion molecules. It is known that adhesion molecules are essential for an interaction between cytotoxic T lymphocytes (CTL) and their target cells. As mentioned above, Zarling, et al. have shown that HIV-infected humans, but not HIV-infected chimpanzees, have circulating CTL that lyse uninfected CD4+ T cells. Because HIV-infected chimpanzees do not develop HIV disease, autoreactive CTL directed against healthy CD4+ cells, and other adverse CTL effects, may account for the emergence of disease in HIV-infected humans.

BRIEF SUMMARY OF THE INVENTION

The present invention envisions treatment of HIV infection by infusing a dose of monoclonal antibodies (MAbs) to inhibit overproduction of Lymphocyte function-associated molecule 1 (LFA-1) on CD8 cells. Monoclonal antibodies that inhibit overproduction of LFA-1 are referred to herein as "anti-LFA-1 MAbs". The LFA-1 adhesion molecule has an alpha ($\alpha$) chain and a beta ($\beta$) chain. The a chain includes approximately 100 binding sites, as does the $\beta$ chain. LFA-1$\alpha$ thus presents a plurality of binding sites for MAb's, as does LFA-1$\beta$. Experimental results have now shown that at least one anti-LFA-1$\alpha$ MAb (namely, S6F1) is useful for treating a patient having suppressed immune function from HIV infection in order to inhibit overproduction of LFA-1 on CD8 cells. In addition, experimental results have shown that anti-LFA-1$\alpha$ MAb's are not the only MAbs useful for this purpose. In particular, an anti-LFA-1$\alpha$ MAb (namely, TS1/18) has shown efficacy according to the preferred treatment method. Thus, overproduction of LFA-1 on CD8 cells has been established for patients through infusing of S6F1 (which binds to four (4) distinct sites on the alpha chain) and through infusing TS1/18 (which binds to at least one specific site on the beta chain).

Thus the present invention envisions infusing a dose of at least one MAb selected from a group of MAbs that specifically bind to any LFA-1$\alpha$ binding site and any LFA-1$\beta$ binding site.

HIV vaccine studies have shown that reducing CTL's causes the host's CD4 count to go up. The present invention is based on the deduction that the reason CD4 counts go down in the first place as a result of HIV infection is because among the various types of CTL's, there must be an anti-self, anti-CD4 CTL. Thus, the maladaptive CTL synthesized by humans is the factor that transforms HIV infection into a catastrophic disease. This is confirmed by the work of Zarling et al, who found that because HIV infection does not lead to any serious disease in chimpanzees, it is the anti-self, anti-CD4 suicide cell, rather than HIV itself, that is directly responsible for the disease associated with HIV infection in humans.

The destructive role of the anti-self, anti-CD4 cytotoxic T-lymphocyte is overcome according to the teachings of the present invention through the use of monoclonal antibodies directed against one or more particular antigens on the anti-self, anti-CD4 killer cell or antigens on the lytics produced by such killer cell. Through infusion of particular monoclonal antibodies directed against such antigens, the anti-self, anti-CD4 cytotoxic T-lymphocytes or their lytics, as the case may be, are neutralized to prevent an HIV positive patient from developing AIDS or to cure the disease itself if the disease has sufficiently advanced into AIDS. In addition, use of adhesion antibodies neutralizes cells producing HIV to improve the health of infected patients.

More specifically, as noted above, one embodiment of the present invention utilizes monoclonal S6F1 mouse antibodies (S6F1 MAb) directed against an adhesion epitope of LFA-1. An infusion of S6F1 MAb elicits an immune response that is believed to remove HIV-producing CD4+ T lymphocytes from the peripheral blood of some adults with HIV disease. Lymphocyte trafficking into tissue has been eliminated based on mathematical statistics. Four individuals with early disease were treated in accordance with the present invention. HIV-producing cells were removed by antibody infusion and replaced by single marked (CD4+ CD8−)CD4+ T lymphocytes in all four individuals. The replacement cells circulated while a decrease in serum levels of HIV RNA persisted, thereby indicating that the newly-circulating cells are uninfected. These single-marked cells are functional as evidenced by an improvement in delayed cutaneous hypersensitivity reaction.

It is thus a primary objective of the present invention to provide a method for preventing and/or curing HIV disease by eliminating or neutralizing anti-self, anti-CD4 CTL's or their lytics from the circulating blood of an HIV-infected patient through the infusion of monoclonal antibodies directed against the antigens presented by such cells or their lytics.

These and other objects of the invention are provided in a method which transforms HIV into a nonserious infection. This is accomplished by neutralizing or removing the anti-self, anti-CD4 suicide cell from the circulating blood of an individual infected with HIV or who is at risk of such infection, and by neutralizing or removing HIV-producing cells.

The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention as will be described. Accordingly, other objects and a fuller understanding of the invention may be had by referring to the following Detailed Description of the preferred embodiment.

BRIEF DESCRIPTION OF THE DRAWINGS

For a more complete understanding of the present invention and the advantages thereof, reference should be made to the following Detailed Description taken in connection with the accompanying drawings in which:

FIG. 4 shows mean T cell/mm$^3$ v. weeks since infusion of S6F1 MAb alone according to the present invention;

FIGS. 5(a)–(d) show the results of several patients treated in accordance with the method of the present invention who had a baseline absolute CD4 count greater than 200 cells/mm$^3$;

FIG. 6 shows the results of a patient with advanced HIV disease treated with IL-2 and S6F1 and subsequently with THF in addition to IL-2 and S6F1;

FIG. 7 compares the results of treatment of S6F1 MAb, infusion and infusion with S6F1 MAb, IL-2 and THF;

FIG. 8 illustrates response to a second infusion in accordance with a treatment method; and FIG. 9 shows the arithmetic mean of CD8% and CTL % of T cells for five patients who had single-marked CD8+ T cells.

DETAILED DESCRIPTION OF THE PREFERRED EMBODIMENT

By way of brief background, it is well known that cytotoxic T-lymphocytes ("CTL's") are white blood cells that kill other cells. If a CTL kills foreign cells (such as bacteria, fungus, viruses, cancer or the like), it is deemed a normal cytotoxic T-lymphocyte. On the other hand, if the CTL kills healthy cells of the body that the cell belongs to, it is deemed an "anti-self" cytotoxic T-lymphocyte. In either case, such cells typically function by destroying the cell membrane of the target cell using one or more "lytics", which are known chemical compounds. The process of breaking apart the target cell is referred to as lysis.

CTL's belong to a group of lymphocytes that carry a CD8 antigen. HIV vaccine studies have shown that reducing CTL's causes a host patient's CD4 count to go up. From this evidence, it has now been recognized that the reason CD4 counts go down in the first place as a result of HIV infection is because among the CTL's, there must be an anti-self, anti-CD4 CTL. Thus, AIDS is caused not by the infection itself, but by a white blood cell made in response to the infection.

In accordance with one embodiment of the present invention, S6F1 mouse antibodies (S6F1 MAb) are directed against an epitope of LFA-1. As discussed in Morimoto, et al., "A Novel Epitope of the LFA-1 Antigen which can Distinguish Killer Effector and Suppressor Cells in Human CD8 Cells", Nature, 1987; 330:479–82, this epitope is a ubiquitous human adhesion molecule. It marks cytotoxic CD8+ T lymphocytes, as contrasted with suppressor CD8+ T cells. Proliferation of CD8+S6F1+ T cells is known to be characteristic of progressing HIV disease. It should be noted, however, that the present invention is not limited to the use of mouse antibodies. In accordance with another embodiment of the present invention, LFA-1 and ICAM monoclonal antibodies are also directed against the intercellular adhesion molecules. As discussed herein, other antibodies are also suitable for use in accordance with the present invention.

Figure 1:
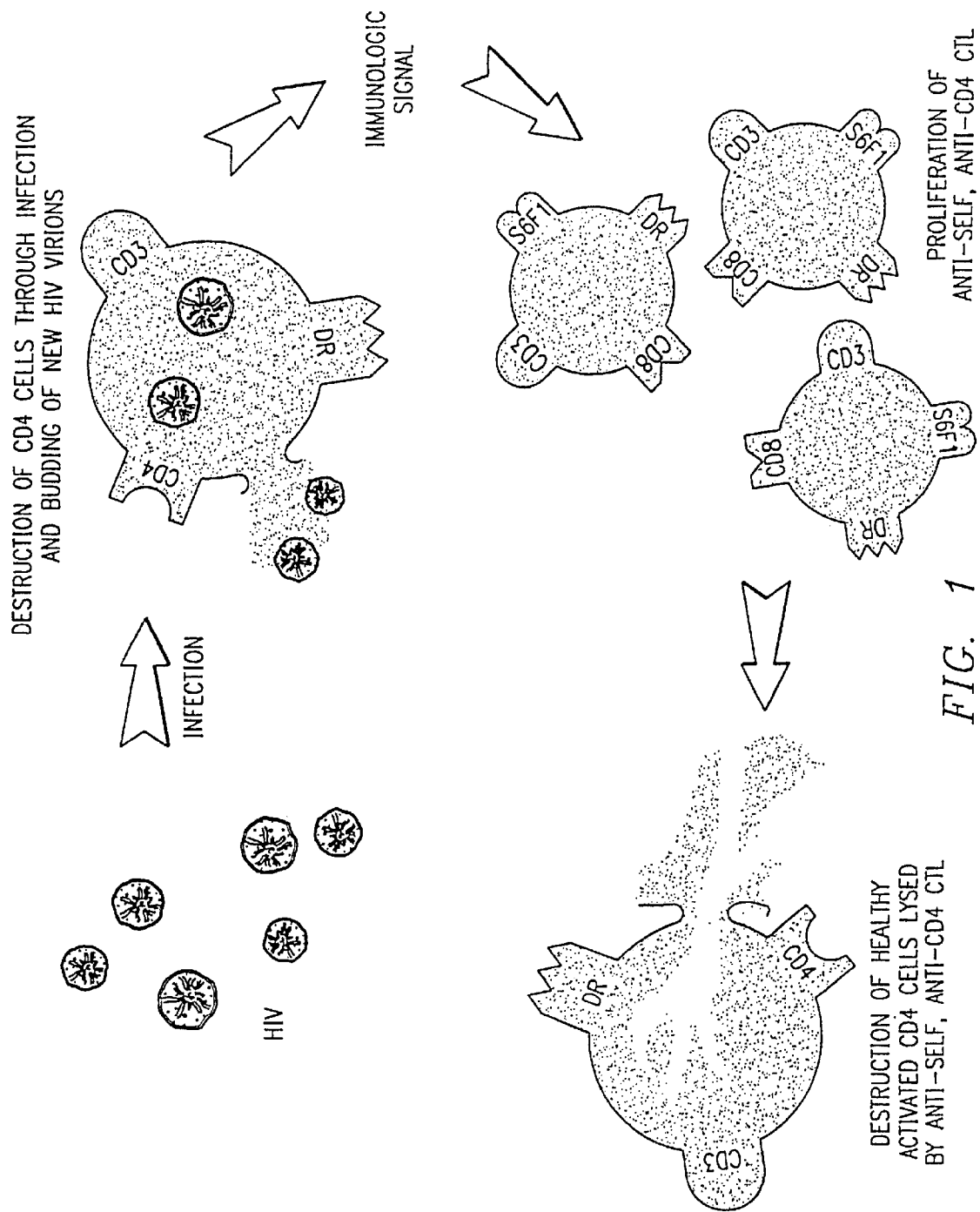
FIG. 1 is a schematic representation of AIDS pathogenesis showing the role of the anti-self, anti-CD4 CTL in the progression of HIV disease into AIDS.

FIG. 1 is a schematic representation of what is believed to be the AIDS pathogenesis. As seen in this figure, the HIV infection leads to the destruction of CD4 cells through infection and budding of new HIV virions. This process generates an immunologic signal that causes the proliferation of anti-self, anti-CD4 cytotoxic T-lymphocytes. As shown in FIG. 1, these cells carry various known antigens including, without limitation, DR, CD8, LFA-1, ICAM and TCR-1. The cells also include one or more lytics which are chemical compounds used to attack the target cell; such lytics also include antigens. The anti-self, anti-CD4 CTL's or their lytics then destroy healthy activated CD4 cells. Thus AIDS is probably caused not by the infection itself but by the white blood cells made in response to the infection.

The present invention overcomes the destructive action of the anti-self, anti-CD4 CTL's or their lytics by infusion of monoclonal antibodies into the bloodstream of the host patient. It also overcomes the deleterious effects of HIV replication. As is known in the art, a monoclonal antibody is an antibody that is made from one cell so that all resulting antibodies are the same.

The standard process of making monoclonal antibodies is described in, for example, Immunology III, by Joseph A. Bellanti (W. B. Sanders, 1985) at pages 99–100, which teachings are incorporated herein by reference. Of course, the particular method for making the monoclonal antibodies is not limited to such technique and it is envisioned that any technique for making such antibodies is within the practice of the invention. The antibodies are designed to be directed toward a particular antigen on the anti-self, anti-CD4 CTL or an antigen on lytics produced by such CTL.

Figure 2:
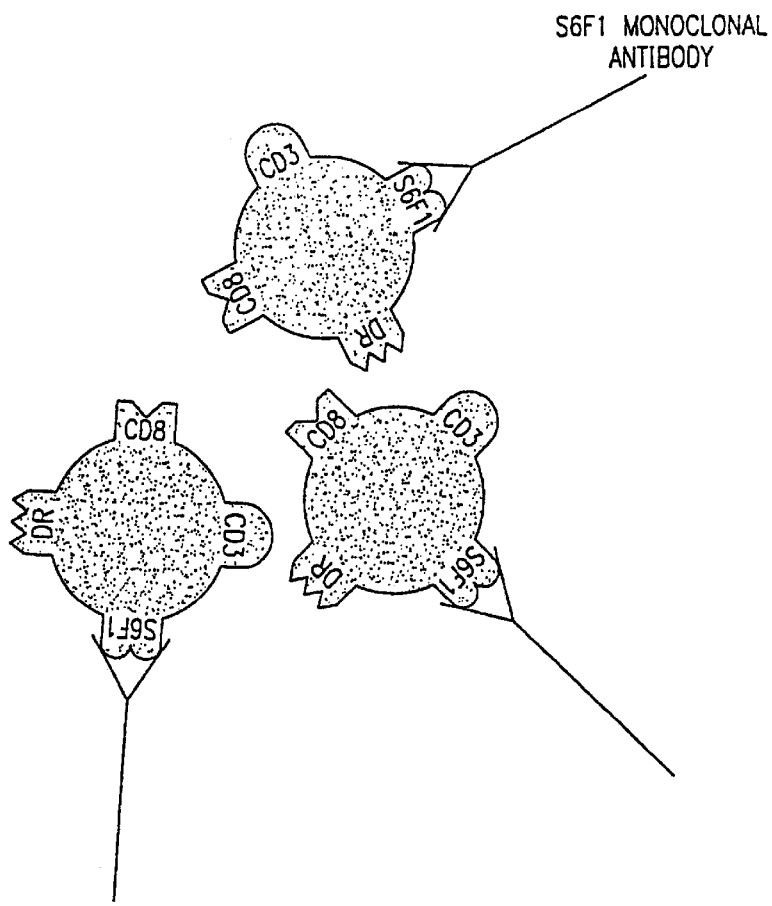
FIG. 2 is a schematic representation of a S6F1 monoclonal antibody attached to the S6F1 antigen on the anti-self CTL according to the teachings of the present invention.

Referring now to FIG. 2, a representation is shown of the particular treatment method. As seen, monoclonal antibodies directed against a specific antigen, in this case the S6F1 antigen on the anti-self, anti-CD4 CTL, are produced in the conventional manner and infused into the bloodstream of the host patient. The particular monoclonal antibody is shown attached to the antigen. Such mating flags the immune system and triggers a known immunological response to cause the body to attempt to neutralize the cells. In this manner, the anti-self, anti-CD4 CTL cell is neutralized. A similar mechanism would be used if the particular monoclonal antibodies were directed to an antigen on a lytic produced by the CTL cell.

According to the invention, monoclonal antibodies are directed to one or more of the antigens on the CTL cell or its lytics. Under some circumstances, it may be desirable to limit the type of monoclonal antibodies to certain specific antigens. Or, it may be desirable to treat the patient first with a particular monoclonal antibody and then use another monoclonal antibody later, or to use multiple antibodies simultaneously. Thus, for example, since many cells (besides the CTL) carry the CD8 antigen, it may be desirable to limit use of the CD8 monoclonal antibodies until an initial improvement in the patient's immune system is established through some other antigen target. The present invention is intended to cover all such variations on the sequence and scope of how the particular monoclonal antibodies are infused.

Although not meant to be limiting, the monoclonal antibodies are preferably infused once per month over a period of between 10 minutes in accordance with one embodiment of the invention. The amount of antibodies should typically be about 0.1 milligrams per kilogram of the patient's body weight. The daily regimen is preferably repeated as needed to maintain an effective immune response. As used herein, an effective immune response will typically mean that the patient's CD4/CD8 ratio is returning to normal, accepted levels, that the patient's skin has an improved delayed cutaneous hypersensitivity reaction and/or there is an improvement in HIV-related signs and symptoms. Thereafter, maintenance treatments may be required depending on the course of the infection or disease. Preferably, the patient's blood should be measured on a monthly basis to track the progress of the treatment. Although not meant to be limiting, the monoclonal antibodies are typically supported in a suitable carrier such as PBS. The infusion may be effected using a conventional syringe and line or infusion pump of known manufacture.

As discussed above, the present invention thus exploits the belief that it is the immunogenic component of the HIV infection that results in the progression of HIV to a fatal disease. The significance of the present invention is that it provides a method of neutralizing the maladaptive CTL (or its lytics) that transform HIV infection into AIDS. Thus according to the invention the HIV disease can be transformed from a non-serious infection, and HIV infection can be prevented from becoming a serious disease, if the suicide cell and/or its lytics are neutralized in, or removed from, an individual infected with HIV or at risk of such infection.

Thus the method transforms HIV infection through the infusion of monoclonal antibodies directed against anti-self CTL's or their lytics. This approach recognizes that monoclonal antibodies have a direct and specific effect against the body of specific antigens. As used herein, S6F1 refers to a mouse antibody directed against an epitope of the human LFA-1 antigen. LFA-1 and ICAM refer to monoclonal antibodies directed against an epitope of the human LFA-1, ICAM-1, ICAM-2 and ICAM-3 antigens. According to the invention, a necessary but sufficient dose of monoclonal antibodies is infused into the bloodstream until anti-self CTL's have been eliminated or neutralized and HIV disease cured, or anti-self CTL's are incapable of proliferating and HIV disease has thereby been prevented, or the replication of new HIV virions has been suppressed or reduced.

The S6F1 and TS1/18 monoclonal antibodies noted in the following experimental section are both directed against an epitope of LFA-1. S6F1 is directed against the alpha ($\alpha$) chain of LFA-1 while TS1/18 is directed against the beta ($\beta$) chain of LFA-1. In particular, S6F1 binds to four (4) specific sites (one of which is also the receptor for a TS1/22 MAb). As shown in the experimental section, monoclonal antibodies that specifically bind to any LFA-1 binding site (whether on the alpha chain or the beta chain) are thus effective in treating and inhibiting disease and symptoms associated with the HIV disease.

Stated differently, the particular MAb itself is not critical (for efficacy of the treatment regimen) provided the MAb specifically binds to at least one binding site on either an alpha or beta chain to thereby inhibit overproduction of LFA-1 on CD8 cells. It is this mechanism (and not necessarily the particular MAb) that provides the signficant advantages of the present invention.

EXPERIMENTAL

Example 1

A patient, infected with the HIV virus for about ten years, had been receiving treatment by injection of his own T cells to achieve a biphasic elevation of the CD4/CD8 ratio. The patient had been responding to such injections for a period of about fifteen months of treatment. At that time, the patient had also been on ddI for approximately two years. However, given the advanced stage of the patients' disease, both of these treatments were no longer providing beneficial results. In fact, HIV could be cultured from his blood cells even when the blood was diluted out to about one part per 3,120. Even at such dilution, the p24 antigenemia, which is a measure of HIV activity, was quite high at about 300 pg/ml.

The patient was then treated in accordance with the method of the present invention. In particular, the patient was given about 68 mg of S6F1 antibodies over a period of 14 days. The 68 mg corresponded to 1 mg/kg of the patient's body weight. A few days after completing the treatment, the AIDS virus could no longer be cultured from the circulating blood cells of the patient. Thus, treatment in accordance with the present invention reduces viral load in the circulating blood of patients with long-term HIV infection.

The speed with which infectious cells disappeared from the patient's circulating blood suggests that some phagocyte may have destroyed the infected cells. In fact, the patient experienced a marked increase in monocytes during treatment, and the treating physician believed at the time, that these monocytes could be destroying the infected cells. However, the antiviral effect could also be due to the blockage of the adhesion pathway needed for communication between antigen presenting cells, thus rendering HIV-infected cells noninfectious.

Depending on the progression of disease in the individual and other factors, the dosage range varies from about 0.01 to about 1.0 mg/kg body weight for a patient treated in accordance with the present invention.

This treatment regimen establishes the efficacy of anti-LFA-1α MAbs.

Example 2

Patient MW-64 had a CD4+ count of 290 and a CD4/CD8 ration of 0.13 (NGI labs); prior to his first infusion of 14 milligrams of TS1/18 monoclonal antibodies. His CD4+ cell count rose to 460 and his CD4/CD8 ration rose to 0.20 just four weeks after the first infusion. It is crucial to note that MW-64 was stable on antiretrovirals for six months preceding the infusion of TS1/18 monoclonal antibodies and did not introduce any new therapies during this interval. There was also some suggestion of a return of some cell mediated immunity in MW-64 since the first infusion, with increased reactivity to tetanus toxoid and candida on skin testing. MW-64 has been infected with HIV for twelve years and his CD4+ cell counts have been about 250 for the past two years.

This treatment regimen establishes the efficacy of anti-LFA-1β MAbs.

Example 3

Patient SG-67 had a CD4+ count of 330 and a CD4/CD8 ratio of 0.28 prior to his first infusion with TS1/18 monoclonal antibodies. His CD4+ cell count rose to 530 and his CD4/CD8 ratio rose to 0.56 just four weeks after the first infusion. It is crucial to note that SG-67 was stable on antiretrovirals for four months preceding the infusion of the TS1/18 monoclonal antibodies and no new therapies were introduced during this interval. There is also some suggestion of a return of some cell mediated immunity in SG-67 since the first infusion, with increased reactivity to tetanus toxoid on skin testing. SG-67 has been infected with HIV for eleven years and his CD4+ cell count has hovered around 300 for the past three-and-one-half years.

This treatment regimen further establishes the efficacy of anti-LFA-1β MAbs.

Example 4

Written consent was obtained from six white, male young adult homosexuals with stable HIV disease to participate in the following treatment program. At baseline, the absolute CD4 counts in the six participants ranged from 1–681 cells/mm$^3$. All patients were advised to take acyclovir in the event that treatment might suppress peripheral immunity. Those patients with absolute CD4 counts of less than 500 cells/mm$^3$ were receiving prophylactic treatments to prevent pneumocystis carinii pneumonia (PCP). The patients were receiving a variety of anti-HIV treatments. One patient, however, was naive to all therapies. Two patients were receiving standard antiretroviral drugs, and the three remaining patients were taking investigational drugs.

Antibody Production

One suitable S6F1 clone, S6F1LDB11LDHL10, is disclosed in U.S. Pat. No. 5,002,869 to Dana Faber Cancer Institute. The clone is derived from the hybridation of mouse NS/1-AG4 myeloma cells with spleen cells from BALB/cj mice immunized with the cell line 1670, an immortalized splenocyte population derived from a Herpes virus saimiri strain II infected whitelip tamarin. Monoclonal S6F1 MAb was produced by GMP as cites in BALB/c mice and purified by the aseptic method using a protein G column. Purity was greater than 90% by SDS-PAGE and endotoxin levels were a remarkably low 3 EU/ml by Limulus Amebocyte Lysate (LAL) Pyrote11ôtest. Purified product was provided in aliquots containing 1 mg/ml S6F1 MAb in PBS without preservatives. Boluses of up to about 10 mg/kg produced no evidence of toxicity in Sprague Dawley rats and all organ systems were grossly normal on postmortem examination.

Laboratory Tests

T Lymphocyte Phenotype Enumeration

T cell phenotypes were enumerated by a 3-color flow cytometry gating on CD3+ lymphocytes for accuracy. Some confirmation tests utilized the 2-color method gating on lymphocytes. While not meant to be limiting, flow cytometers such as the EPICS® Profile II available from Coulter Corporation and FACscan® available from Becton-Dickinson are suitable for use in accordance with the method of treatment of the present invention.

HIV RNA

HIV RNA was measured by polymerase chain reaction (PCR) in accordance with Muul, "Current Status of Polymerase Chain Reaction Assays in Clinical Research of Human Immunodeficiency Virus Infection", *AIDS Updates*, 1990; 3:1–19. Viral RNA was extracted from the serum specimen by a modified Chromszinsky method using guanidine/plant chloroform. The purified RNA was divided into two portions and each was randomly mixed with hexamer primers. Separate but identical reverse transcriptase reactions were then carried out for each portion. Each resultant cDNA portion was subsequently amplified by multiple Hot Start Polymerase Chain Reaction amplification cycles using two separate primer sets. The post amplification reaction material then underwent agarose gel electrophoresis and Southern blotting using nylon membranes and specific transfer buffers. These were UV crosslinked, prehybridized, probed with fragment-specific dUTP digoxigenin probes, stringency washed, and immunostained using alkaline phosphatase conjugated digoxigene-specific antibody, X-phosphatase (an insoluble colorogenic alkaline phosphatase substrate) and nitroblue tetrazolium (NBT). This resulted in quantification of the RNA in copies per milliliter. Duplicate samples were run as one batch in parallel with 50% positive and negative controls. Negative controls were of two types: blanks with no genetic material and cells which were known to be HIV-1 negative. Discrete RNA and DNA material from HIV-1 served as the positive controls. Negative and positive controls were interposed between every sample.

Laboratory Controls

Critical data points were confirmed by parallel testing in 2 or 3 independent blinded laboratories.

Delayed Cutaneous Hypersensitivity

Figure 3:
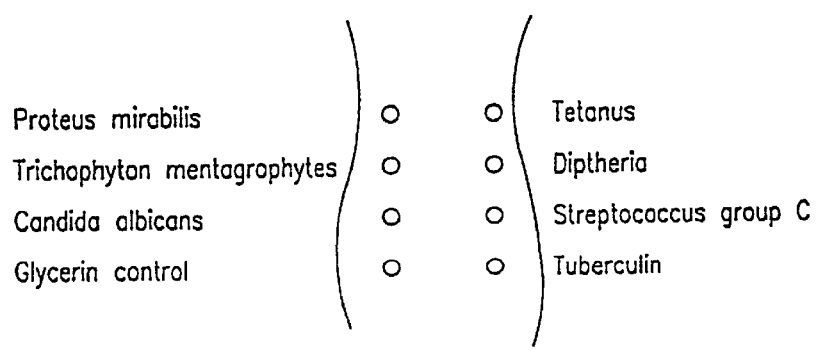
FIG. 3 illustrates the placement of antigen and control on a forearm for a skin test to measure delayed hypersensitivity reaction in accordance with the present invention.

Cell mediated immunity was evaluated with the Multitest CMI® skin test for delayed cutaneous hypersensitivity reaction in accordance with the procedure and materials of Connaught Laboratories, Inc. This test is utilized to challenge the skin of the anterior forearm with 7 antigens and a glycerin control as shown in FIG. 3. According to the package insert, the response to an antigen is positive if, and only if, it produces an induration with a mean axis of greater than or equal to 2 mm. Among normal controls, the mean number of positive responses is 4.5. This, and similar tests, have been found reliable in evaluating cell-mediated immunity in lung cancer patients treated with radiotherapy, patients admitted to intensive care units, patients undergoing gastrointestinal surgery and debulking of kidney tumors, patients with HIV infection, and patients with diabetes, bronchial asthma, chronic hepatitis, and other diseases. Reliability has been assessed for both inter-readers and intra-readers. Significantly, the use of this test has been shown to have no effect on blood lymphocyte counts or functions. Although repeated testing such as once every month or two for six months, can produce detectable changes in the results, these changes are insignificant and minimal and do not preclude paired testing to follow immunocompetence. It is standard practice to use serial tests to follow changes in cell-mediated immune function.

Infusion

Each patient was infused with about 7 mg (approximately 0.1 mg/kg) of S6F1 mAb over a period of about ten minutes. Ibuprofen, 400 mg every 4 hours for 12 hours, was prescribed the day of infusion to prevent serum sickness (cytokine release syndrome). Subjects were followed for the first six weeks and continue to be monitored monthly. Reinfusions are administered as needed, which is generally about every 1–2 months.

Results

Within two weeks following infusion of S6F1 MAb, three out of five patients or 60% of those treated with S6F1 MAb, but not Il-2, experienced a drop in HIV RNA greater than or equal to an order of magnitude ($\log_{10}$ 1st RNA- $\log_{10}$ 2nd RNA greater than or equal to 1) as measured by PCR. In all three patients, this decrease in viral RNA was correlated with a transient drop in CD4 cells, which was observed in 4 of the 5 patients or 80% of those treated. This is to be expected as HIV is intracellular. Thus, a reduction in viral burden should involve clearing of some CD4 cells. In all cases, there was a subsequent rebound of circulating CD4+ T lymphocytes by the third week following infusion of S6F1 MAb. As illustrated in FIG. 4, there was a correlated improvement in the skin test for the delayed hypersensitivity reaction by the fifth week. Suppression of viral RNA persisted well beyond the rebound of CD4 cells. While the mechanism is not yet certain, the results indicate that HIV-producing cells are replaced by uninfected cells.

Patients with Early HIV Disease

Figure 5B:
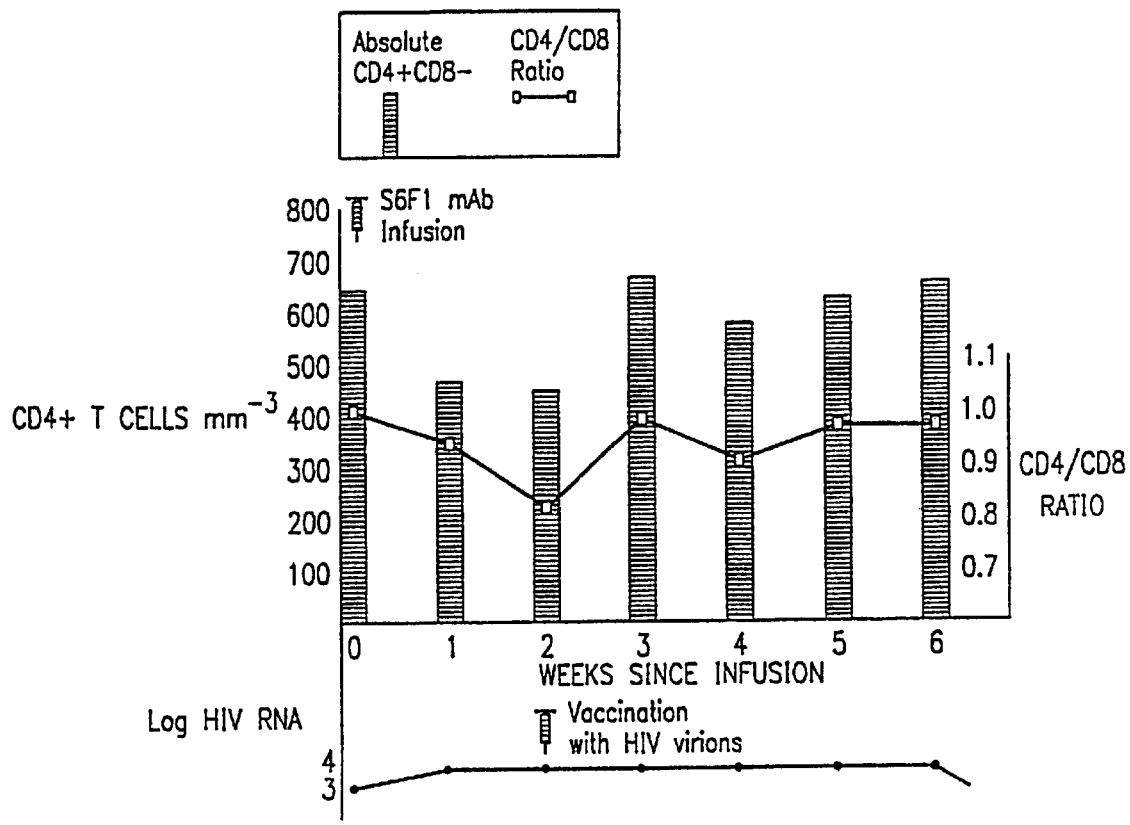
Figure 5C:
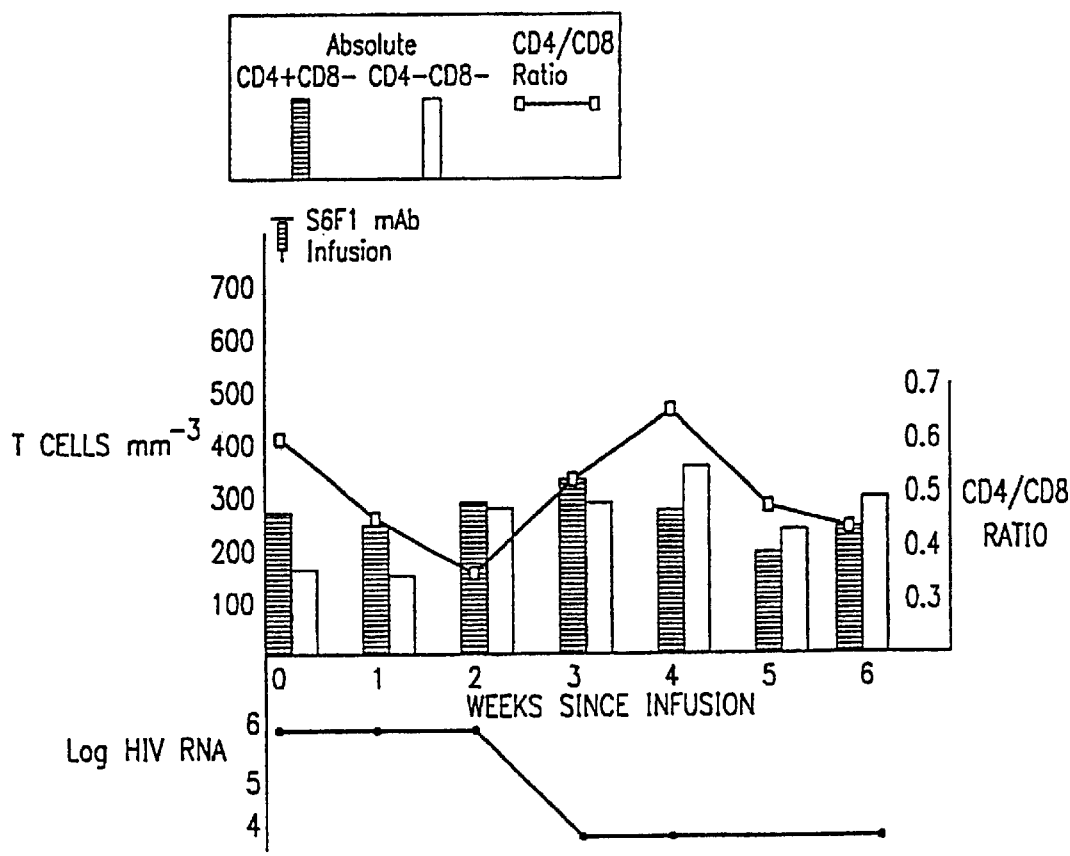
Figure 5D:
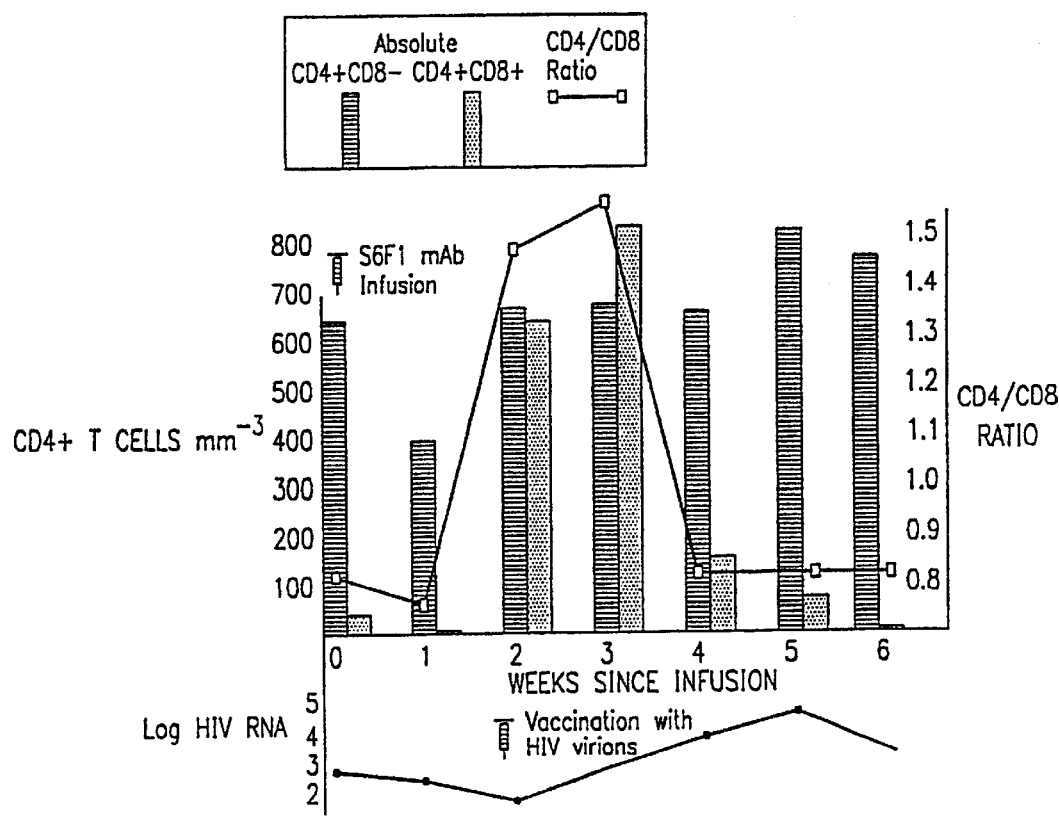

FIGS. 5(a)–(c) show the results for three patients with early disease whose rebound of CD4 cells included only mature, single-marked CD4+CD8– T lymphocytes. FIG. 5(d) illustrates the results of another patient with early HIV disease whose rebound included both single-marked CD4 cells and double-marked CD4+CD+ T lymphocytes. Five weeks after infusion of S6F1 MAb, this patient's double-marked cells were replaced by single-marked cells. One month after infusion, this patient had a transient increase in HIV RNA because he was vaccinated with inactivated HIV virions while participating in another study. Although immunization may generally raise viral burden, HIV RNA will necessarily increase when a patient is infused with HIV virions. All four of these patients exhibited an improvement in the skin test for delayed hypersensitivity reaction. As shown for example by FIG. 5(a), this improvement in delayed cutaneous hypersensitivity is sometimes dramatic.

Patients with Advanced HIV Disease

FIG. 6 illustrates the results for a patient with more advanced HIV disease. This patient's rebound included only double-marked CD4+CD8+ T lymphocytes. Unexpectedly, these cells replaced all other T cell phenotypes. As shown by the histograms in FIG. 6, it is believed that the double-marked cells were early thymocytes. This is supported by the finding that they were also double-marked for CD1 and 3A1. HIV infection has shown to inhibit IL-2 production, in part because of cross-reacting antibodies. Deficient IL-2 has been implicated in causing HIV-associated CD4+ T lymphocytopenia and impaired T helper function. Thymic humoral factor (THF) has been reported to increase CD4 count and improve skin reactivity. This patient was subsequently treated with twice daily subcutaneous injections of 180,000 units of IL-2 for 14 weeks, together with intramuscular injections of 2.17 micrograms THF for the first 2 weeks, and then three times per week for twelve weeks. As illustrated in FIG. 6, this adjunctive therapy caused his double-marked cells to be replaced by single-marked CD4+ CD8– T cells.

FIG. 7 shows the results of a patient who had no detectable single-marked CD4+CD8–T lymphocytes. This patient was treated from the beginning with an infusion of S6F1 MAb and a regimen of rIL-2 plus THF. By the fourth week following initiation of treatment, a modicum of single-marked CD4+CD8 – cells could be detected in this patient's peripheral blood, although he primarily proliferated double-negative CD4–CD8– T lymphocytes. By the fifth week, these double-negative cells amounted to a significant population. Despite prophylaxis with aerosol pentamidine, this patient developed a mild case of PCP at week 5, thereby indicating that double-negative CD3+CD4–CD8– T lymphocytes may offer little protection against opportunistic infections. This patient had a 2-log increase in HIV RNA, a known effect of IL-2 in HIV infected individuals.

Reproducibility

In order to determine whether the effects of S6F1 MAb are reproduced by reinfusion, the patient illustrated in FIG. 5(a) was reinfused with 7 mg of S6F1 MAb 9 weeks after receiving the first infusion. As shown in FIG. 8, this patient's response to the second infusion included a robust rebound of CD4 cells, and the brief appearance of double-marked cells as compared to FIG. 5(d). It should be noted that the initial drop in CD4 cells did not occur since his HIV RNA did not decrease and continued to be suppressed as compared to baseline.

CD8+ Cells and CTL

As shown in FIG. 9, S6F1 MAb produced only a transient drop in the percentage of CD8+ cells that were cytotoxic (CD3+CD8+S6F1+) during week 2.

Safety

Antibody infusion was well tolerated and no adverse reactions were observed, except a mild allergic reaction in one patient. However, transient mood changes were observed in some patients and could be attributed to cytokine release.

It is currently uncertain whether immunocompromised HIV patients may develop human anti-mouse antibodies (HAMA), which can limit the efficacy of anti-CD3 antibodies used in renal transplantation. However, in order to test whether such patients may develop HAMA, a custom ELISA plate was used to test a patient for HAMA. The patient was not one of the six patients discussed in Example 2 above, but had previously received 68 mg S6F1 MAb over 14 days as discussed above in Example 1. No HAMA was detected. The patient was reinfused using a single dose of 7 mg as described in Example 2. At the time of reinfusion, the patient had a marked CD4+ T lymphocytopenia and CD8+ T lymphocytosis. Because of this, the patient was also treated with THF. IL-2 was not used because the patient discussed above in Example 2 and whose results are shown in FIG. 6 did not exhibit replacement of double-marked T cells when he was administered S6F1 MAb followed by IL-2 alone. Also, IL-2 appeared to increase viral load in another patient as illustrated in FIG. 7. Within two weeks of being reinfused, the patient being evaluated for HAMA had 95% of his circulating T cells double-marked for CD4 and CD8, and the remaining 5% were single-marked as compared with the results in FIG. 6, thereby indicating a response to MAb infusion uninhibited by HAMA.

Nonetheless, there are known techniques to eliminate the heavy chains in antibodies which are known to be responsible for causing HAMA to develop. Moreover, these techniques leave the light chains, which produce the benefit of treatment with antibodies, intact. Accordingly, HAMA may also avoided by removing the heavy chains in antibodies.

Other antibodies are suitable for use in the present invention. For example, it is known now to produce artificial antibodies from peptides and the like. These antibodies may be used in the present invention so long as the intended results are obtained. Additionally, human antibodies are suitable for use in accordance with the invention.

It is known that CD8+ T lymphocytes have been shown to suppress HIV replication in vitro. The ability of ex vivo blood to demonstrate this effect correlates with the clinical status of HIV patients. On the other hand, the selective depletion of CD8+ T cells from the circulating blood of HIV patients has a beneficial effect. General evidence in this regard has led to the advent of the "homeostasis" hypothesis of HIV disease. The results shown in FIG. 6 suggest that the CD8+ T cell significance is not yet completely understood. This patient had no circulating CD8+CD4− T lymphocytes at all for greater than three months and there were no apparent clinical consequences.

CD4+ T Lymphocyte Counts

The results shown in FIG. 5(b) are particularly important since a significant increase in skin reactivity occurred without a decrease in HIV RNA and without an increase in CD4 count above baseline. The drop in CD4 count over the first two weeks suggests that HIV-transformed cells were cleared despite the lack of decrease in HIV RNA. The latter may have been due to an unrelated HIV vaccine the patient received two weeks into treatment in accordance with the present invention. As noted above, an infusion of HIV virions may increase HIV RNA. In any event, these results demonstrate that the cell mediated immunity improves significantly without an increase in CD4 count. It is well known that CD4 cell function, and not simply CD4 count, plays an important role in immunocompetence.

Double-Marked CD4+CD8+ T Lymphocytes

A flow cytometer will count any lymphocyte that bears the CD3 (T cell) and CD4 markers as a CD4+ T lymphocyte. This includes both mature, single-marked, CD4+CD8− T lymphocytes and immature double-marked, CD4+CD8+ T lymphocytes. The patient whose results are shown in FIG. 6 for example, could thus be interpreted to have had 900 CD4 cells early in treatment. Although this was true, the patient also had 900 CD8 cells and a total of 900 T cells, meaning that all of his T cells were both CD4 cells and CD8 cells. It should be noted that double-marked CD4+CD8+ T lymphocytes proliferate in the natural course of HIV disease. To differentiate this phenomenon, a 3-color flow cytometry should be used rather than the 2-color flow cytometry used in routine clinical practice.

Immature CD4+CD8+ thymocytes express only a few molecules serving as T cell receptors (TCR), and they have minimal capacity for transducing intracellular signals. It is therefore not surprising that improvements were not observed in delayed cutaneous hypersensitivity in patients circulating only double-marked CD4+CD8+ T cells. The inhibition of TCR on these double-marked cells appears to be mediated by mature CD4+ T cells. This may explain a dim fluorescence of CD3 receptors that are sometimes observed as a transient effect when mature CD4 cells rebounded.

Double-Negative CD4−CD8− T Lymphocytes

The double negative T cells shown in FIGS. 5(c) and 7 are important because the role of double-negative TcRgd+ lymphocytes in HIV disease has been the subject of considerable debate and speculation. For example, DePaoli, et al., "A Subset of Gamma Delta Lymphocytes is Increased During HIV-Infection", *Clin Exp Immunol.*, 1991; 83:197–91; Margolic, et al., "Flow Cytometric Analysis of Gamma-Delta T Cells and Natural Killer Cells in HIV-1 Infection", *Clin Exp Immunol.*, 1991; 58:126–38; and Autran, et al., "T Cell Receptor Gamma/Delta Lymphocyte Subsets During HIV-1 Infection", *Clin Exp Immunol.*, 1989; 72: 206–10 report an increase in these cells while Hermier, et al., "Decreased Blood TcRgd+ Lymphocytes in AIDS and p2Y-Antigenemic HIV-1 Infected Patients, *Clin. Immunol. Immunopathol.*, 1993; 69: 248–250 report a decrease. These cells sometimes reflect secondary infections. Even in immunocompetent patients, TcRgd+ lymphocytes were found to be increased in the course of several infections such as toxoplasmosis (See, Scalise, et al., "Lymphocytes Bearing the Gamma-Delta T-Cell Receptor in Acute Toxoplasmosis", *Immunology*, 1992; 76: 668–70). This may explain the double-negative cells illustrated in FIG. 7 because the patient had evidence of opportunistic infection. However, the double-negative cells shown in FIG. 5(c) are unclear at this time. In one study, high percentages of TcRgd+ cells were found in HIV-infected patients for whom secondary infections appear to have been eliminated. Thus, these cells may be related to peculiar immunopathologic processes associated with HIV infection.

It should be noted that the flow cytometry may produce spurious reports of double-negative cells on blood specimens collected within a few days of S6F1 MAb infusion. Apparently this is due to competitive interference between freely circulating S6F1 MAb and the diagnostic MAb used for flow cytometry.

Pathogenesis of HIV Disease

The present invention establishes that there are two distinct pathogenic elements in HIV disease. Initially, cell-mediated immune function is probably degraded by the colonization of CD4 cells by HIV with a resulting impairment of cell function. At this early stage, immunodeficiency may be reversible if the HIV-producing cells are neutralized. The infected cells that have been neutralized are then replaced by mature, healthy uninfected CD4 cells. At a later stage of the disease, however, the host is unable to replace infected cells with mature, single-marked CD4+CD8− T lymphocytes, as illustrated in FIGS. 6 and 7. This is probably due to lymphatic architecture, which becomes damaged as HIV disease progresses. As further shown in FIGS. 6 and 7, this patient had a significant increase in mature circulating CD4 cells after receiving rIL-2 and THF. Anti-adhesion antibodies can be used to neutralize HIV-producing cells from the lymph nodes, thereby preventing or retarding damage to the follicular dendritic architecture. Furthermore, this may retard the spread of HIV infection since cell-to-cell infection occurs primarily in the lymph nodes during the clinically latent period of infection.

The effectiveness of Applicant's method using LFA-1, ICAM-1, ICAM-2 AND ICAM-3 monoclonal antibodies on CD4+ T lymphocyte depletion is further illustrated in Butini, et al, "Intercellular adhesion molecules (ICAM)-1, ICAM-2 and ICAM-3 function as counter-receptors for lymphocyte function-associated molecule 1 in human immunodeficiency virus-mediated syncytia formation", *European Journal of Immunology*, 1994, Vol. 24, pp. 2191–2195. The results of these experimentations are incorporated herein by reference. The monoclonal antibodies utilized within the experiments discussed in the Butini article included the hybridoma cell lines for TS1/22 and TS1/18 monoclonal antibodies, directed against LFA-1 antigens. RR1/1, CBR-IC2/1 and CBR-IC2/2 monoclonal antibodies were directed against ICAM-1 and ICAM-2 antigens. CBR-IC3/1 and CBR-IC3/2 monoclonal antibodies were directed against two different isotopes of ICAM-3 antigens.

Particularly with respect to CD4+ T lymphocyte depletion, the treatment of cultures with LFA-1 monoclonal antibodies significantly reduced the amount of CD4+cell depletion with respect to the treated cultures. The CD4+T cells remain completely viable until day ten after infection and showed only a minor depletion of CD4+ T cells (approximately 20%) at day 19. In untreated cultures, a decrease in CD4+ T cell viability was evident at day 10, and by day 16 the depletion of CD4+ T cells was 80%. Similar results were obtained in cultures treated with ICAM-1, ICAM-2, and ICAM-3 monoclonal antibodies. However, the depletion protection of day 19 was not as high as that achieved with LFA-1 monoclonal antibodies and the depletion was in the 50% range.

An alternative embodiment of the present invention also serves as a preventative measure for health care workers. In particular, an HIV-infected individual requiring invasive medical or dental procedures, undergoes treatment in accordance with the present invention prior to such surgery or procedures. In this manner, infectious cells in the circulating blood of the HIV-infected individual are reduced, thereby protecting health care workers involved with the surgical procedures by reducing the possibility of HIV exposure.

It should be appreciated by those skilled in the art that the specific embodiments disclosed above may be readily utilized as a basis for modifying or designing other techniques or processes for carrying out the same purposes of the present invention. Thus, for example, other delivery vehicles or techniques may be used for delivering the monoclonal antibodies to the bloodstream. Implementation of the treatment method has been based on antibodies from the S6F1 and TS1/18 clones. It should follow that any monoclonal antibody that inhibits the same immunological pathway will provide the same therapeutic benefits in HIV-infected individuals. It should also be realized by those skilled in the art that such equivalent processes do not depart from the spirit and scope of the invention as set forth in the appended claims.

What is claimed is:

1. A method for increasing the delayed-type hypersensitivity response in a patient having suppressed immune function comprising the steps of:
    (a) infusing a dose of a monoclonal antibody selected from the group consisting of monoclonal antibodies specifically binding to LFA-1α binding sites and LFA-1β binding sites on CD8$^+$ lymphocytes, said dose being between about 0.1–1.0 milligrams of said monoclonal antibody per kilogram of the patient's weight; and
    (b) repeating said infusion as necessary to increase the delayed-type hypersensitivity response in the patient.

* * * * *